United States Patent
Ferguson

(10) Patent No.: US 11,395,733 B1
(45) Date of Patent: Jul. 26, 2022

(54) METHOD OF FABRICATING SEAMS IN A BIOPROSTHETIC HEART VALVE

(71) Applicant: RIVERPOINT MEDICAL, LLC, Portland, OR (US)

(72) Inventor: Patrick Joseph Ferguson, Portland, OR (US)

(73) Assignee: RIVERPOINT MEDICAL, LLC, Portland, OR (US)

( * ) Notice: Subject to any disclaimer, the term of this patent is extended or adjusted under 35 U.S.C. 154(b) by 44 days.

(21) Appl. No.: 16/892,756

(22) Filed: Jun. 4, 2020

(51) Int. Cl.
*A61F 2/24* (2006.01)
*A61B 17/06* (2006.01)

(52) U.S. Cl.
CPC ...... *A61F 2/2415* (2013.01); *A61B 17/06109* (2013.01); *A61F 2/2418* (2013.01); *A61F 2220/0075* (2013.01)

(58) Field of Classification Search
CPC ............. A61F 2/2415; A61F 2/2418; A61F 2220/0075; A61F 2/24; A61B 17/06109; A61B 17/06; A61B 2017/06028; A61B 2018/1425; A61B 17/06066; A61B 17/04; A61B 17/34; D05B 85/00; D05B 85/02; D05B 85/08; B21G 1/00
See application file for complete search history.

(56) References Cited

U.S. PATENT DOCUMENTS

| | | | |
|---|---|---|---|
| 4,680,031 A * | 7/1987 | Alonso | A61F 2/2409 623/2.13 |
| 5,263,974 A | 11/1993 | Matsutani et al. | |
| 7,977,603 B2 | 7/2011 | Matsutani et al. | |
| 10,603,164 B2 | 3/2020 | Girard et al. | |
| 2019/0008513 A1 | 1/2019 | Ishida | |
| 2020/0015855 A1 | 1/2020 | Shiono et al. | |
| 2021/0196456 A1* | 7/2021 | Cody, III | D05B 23/00 |

FOREIGN PATENT DOCUMENTS

| | | |
|---|---|---|
| EP | 1988835 B1 | 11/2008 |
| KR | 101279278 B1 | 6/2013 |

\* cited by examiner

*Primary Examiner* — Paul B Prebilic
(74) *Attorney, Agent, or Firm* — Timothy E. Siegel Patent Law, PLLC; Timothy E. Siegel

(57) ABSTRACT

A method of sewing preserved animal tissue to a manmade work piece that forms a part of a prospective bioprosthetic heart valve. The method utilizes a needle having an attached suture length and also having a relative object visibility of less than 0.8 relative to a standard straight surgical needle. Also, this needle has a volume of less than 7 mm$^3$ and a surface area of less than 70 mm$^2$, is formed entirely of 300 series stainless steel, and has an eye, and the suture length is threaded through the eye. The needle having an attached suture length is used to manually sew the animal tissue to the manmade work piece that forms a part of the prospective bioprosthetic heart valve, while maintaining sufficient optical closeness to maintain the visibility of the needle.

20 Claims, 1 Drawing Sheet

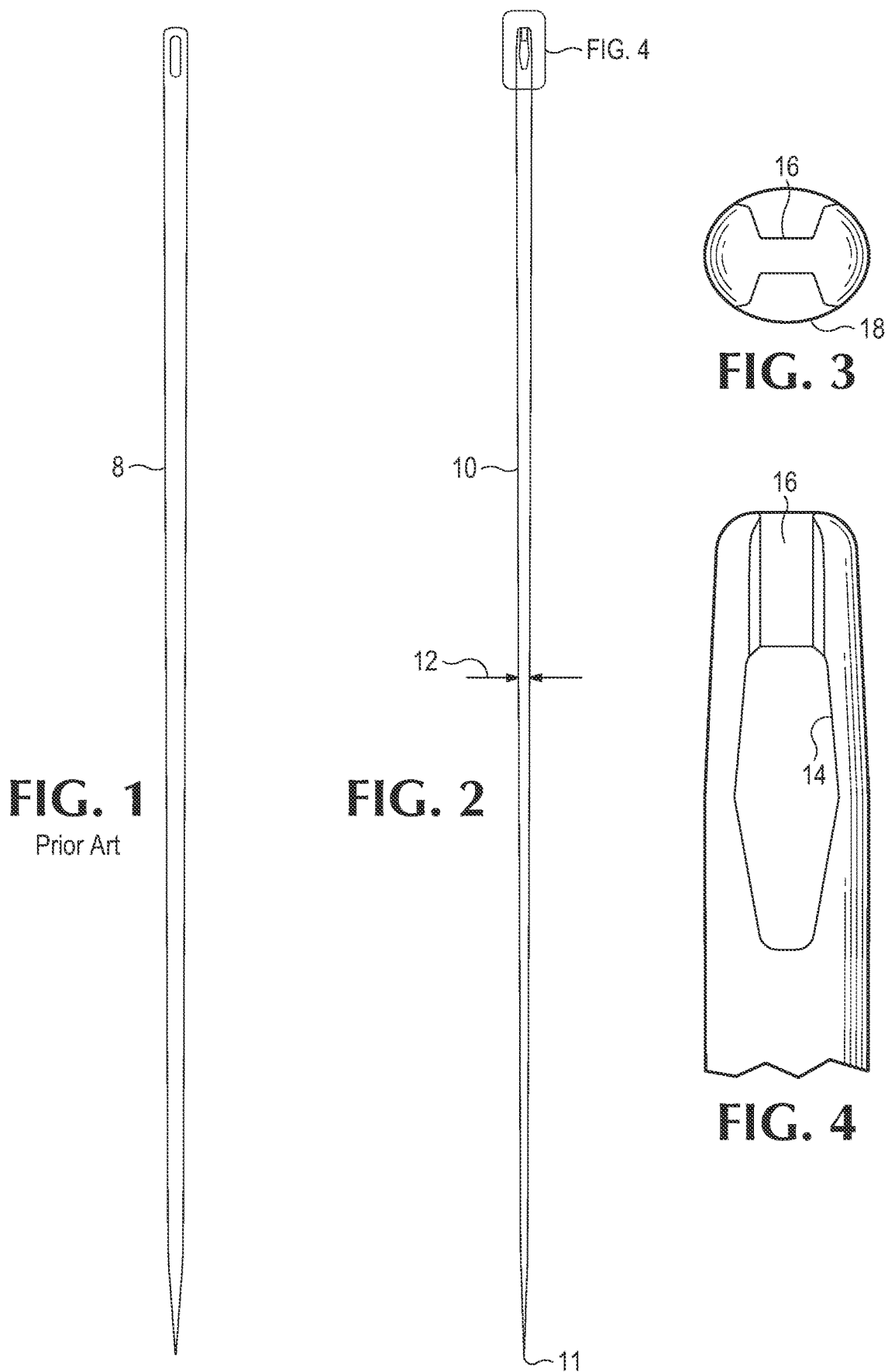

METHOD OF FABRICATING SEAMS IN A BIOPROSTHETIC HEART VALVE

BACKGROUND OF THE INVENTION

The manual labor of producing a bioprosthetic heart valve is challenging. In the manufacturing process, tissue from a bovine pericardium or a porcine heart valve is sewn onto manmade materials, such as a fabric-covered polymeric or metal stent. The animal tissue tends to be tough, so that pushing a currently-available needle through this tissue is a challenge. As a result, the manufacturing personnel are not infrequently diagnosed with repetitive motion work injury, such as carpal tunnel syndrome, which may be career ending for the individual and result in a slow-down in production. Finding a candidate for doing the fine manual work is challenging and training a new worker is time consuming.

The act of drawing a needle through tissue, involves a first act of puncturing the tissue with the needle point, and the pushing the needle through, which is resisted by the friction between the needle surfaces and the tissue. The more force that is required for either or both of these tasks, the greater the amount of potential trauma to the tissue, possibly resulting in a product and patient outcome that is suboptimal. A silicone-coated needle could help to reduce the friction of the needle being pulled through the tissue. Unfortunately, the use of this type of needle is not permitted in the process, due to the residual silicone that would be left behind.

Currently available needles are categorized as surgical or industrial needles. If industrial needles are used, they must be sterilized in house, an unwanted extra step. Surgical needles are generally specialized and expensive. Further, there is a general requirement for a surgical needle, such as prior art surgical needle 8 (FIG. 1) to have a minimum level of object visibility and flexural strength. If the surgeon cannot see the needle 8, as he performs a surgery, he is in a sense, working blind. As a consequence, there is typically a size minimum for a surgical needle, of about 0.5 mm in diameter, below which a surgeon might not be able to see the needle he is manipulating, as in most surgeries a surgeon must be a minimum of about a foot from the tissue he is sewing. It is also notable that a surgeon spends less of his time actually sewing than a manual worker constructing artificial heart valves, so the issues of repetitive action injuries are less severe. Further, living tissue is generally less tough than tissue harvested from a mammal and then preserved prior to being used as a work piece for the manufacture of an artificial heart valve, so the task of pushing the needle through tissue is less burdensome. It is a true observation that there has never before in human history been a task quite the same as the production of artificial heart valves. For decades, now, these heart valves have been sewn using the best needles available for the task, with the resultant carpal tunnel syndrome being a recognized problem, but with no apparent solution.

Industrial needles and surgical needles are generally made of 400 series stainless steel, and are heat treated. Heat treating increases the strength of a needle, which is an important quality at least for many industrial processes. Some might anticipate that using a weaker needle would risk mishaps with needles possibly snapping under the strain of use. This is certainly the case for many industrial uses, where needle strength is important. Industrial needles must be sterilized after being received into the manufacturing facility.

SUMMARY OF INVENTION

The following embodiments and aspects thereof are described and illustrated in conjunction with systems, tools, and methods which are meant to be exemplary and illustrative, not limiting in scope. In various embodiments, one or more of the above-described problems have been reduced or eliminated, while other embodiments are directed to other improvements.

In a first separate aspect, the present invention takes the form of a method of sewing preserved animal tissue to a manmade work piece that forms a part of a prospective bioprosthetic heart valve. The method utilizes a needle having an attached suture length and also having a relative object visibility of less than 0.8 relative to a standard straight surgical needle. Also, this needle has a volume of less than 7 $mm^3$ and a surface area of less than 70 $mm^2$, is formed entirely of 300 series stainless steel, and has an eye, and the suture length is threaded through the eye. The needle having an attached suture length is used to manually sew the animal tissue to the manmade work piece that forms a part of the prospective bioprosthetic heart valve, while maintaining sufficient optical closeness to maintain the visibility of the needle.

In a second separate aspect, the present invention takes the form of a method of sewing preserved animal tissue to a manmade structure, in the production of a bioprosthetic heart valve. The method utilizes a needle having an attached suture length. This needle has a relative flexural strength of less than half that of a standard industrial needle and has a volume of less than 7 $mm^3$ and a surface area of less than 70 $mm^2$. In the method, the needle having an attached suture length is used to manually sew the animal tissue to the manmade work piece that forms a part of the prospective bioprosthetic heart valve, while not placing so much flexural stress on the needle that the flexural stress causes the needle to deform or break.

In a third separate aspect, the present invention takes the form of a method of reducing incidence of repetitive motion work injuries among workers sewing together artificial heart valves from preserved animal tissue and manmade materials. In the method, special needles are provided. These needles have a relative visibility of less than 0.8 that of standard surgical needles and less than half the strength of standard industrial needles and having a volume of less than 7 $mm^2$. In the method, the workers use the special needles in sewing the bioprosthetic heart valves while maintaining sufficient optical closeness to ensure needle visibility and avoiding placing so much stress on the needles that they break or deform. Consequently, the relatively smaller volume of the special needles reduces the force needed to push the special needles through the preserved animal tissue, thereby reducing repetitive motion work injuries.

BRIEF DESCRIPTION OF DRAWINGS

Various embodiments of the invention are disclosed in the following detailed description and accompanying drawings.

FIG. 1 is a plan view of a prior art surgical needle.

FIG. 2 is a plan view of a bioprosthetic valve implant construction needle, according to the present invention.

FIG. 3 is a top view of the needle of FIG. 2.

FIG. 4 is a detail view of the eye of the needle of FIG. 2.

DETAILED DESCRIPTION AND EMBODIMENTS

The following is a detailed description of exemplary embodiments to illustrate the principles of the invention. The embodiments are provided to illustrate aspects of the invention, but the invention is not limited to any embodiment. The scope of the invention encompasses numerous alternatives, modifications and equivalent; it is limited only by the claims.

Definitions: "relative object visibility" is the distance at which a second object can be seen, relative to a first object, when placed against a white background, with 1000 lux of illumination directed at a circle circumscribed by the object (by the same person). For example, if under those conditions a first object can be seen at 100 feet, and a second object seen only if the viewer is 80 feet away, the second object would have a relative object visibility 0.8 relative to the first object. A "standard straight surgical needle" is one that is 50 mm long and is 0.5 mm in diameter at its lengthwise midpoint, has a total diameter (at greatest thickness—that is where the threading hole is located) of no more than three times its midpoint thickness, and is made of 400 series stainless steel, and that has a metallic color, not having been rendered black. A standard industrial needle is the same but has been heat treated for increased strength. To the extent that these descriptions permit a range of values, the standard straight surgical needle and the standard industrial needle will be considered the one that has the least optical visibility and least flexural strength. The term "optical closeness" is the physical distance, shortened by any magnification used. That is, if the object being viewed appears, after magnification, at the size it would be if were six inches away, it would have an optical closeness of six inches. The term "preserved animal tissue" refers to tissue that has been harvested from an animal and then preserved during shipment so that it is useable when it arrives at factory. Preserved animal tissue is generally somewhat calcified and, therefore tougher, than actual living tissue. The term "preserved" should not be taken to imply any sort of preservation process (other than refrigeration), such as placing the tissue in formaldehyde. The term "volume" indicates the displacement volume, or the amount of water that is displaced by the object, when submerged in a container of water. The term "flexural strength" is proportional to the amount of force which must be applied to the midpoint of a long object that is supported at either end, in order to cause the object to break or permanently deform.

How to make needles of the dimensions disclosed here, is known in the art to needle manufacturers, by beginning with a thin wire, stretching it to a smaller diameter, and forming needles from it, according to well-known manufacturing techniques. It appears however that needles that are very thin, are typically eyeless, perhaps being designed for machine use.

A bioprosthetic heart valve, and methods of manufacture of the same are described in U.S. Pat. No. 10,603,164, which is incorporated by reference as if fully set forth herein.

Numerous specific details are set forth in the following description in order to provide a thorough understanding of the invention. However, the invention may be practiced according to the claims without some or all of these specific details. For the purpose of clarity, technical material that is known in the technical fields related to the invention has not been described in detail so that the invention is not unnecessarily obscured.

Needle 10 includes a point 11, a midpoint 12, an eye 14, and a thinned area 16 above the eye 14 (with the point 11 defining the "bottom" of the needle). The top of the needle defines an oval outline 18, and the needle becomes increasingly round as it extends from top to point 11.

In a preferred method of fabricating an artificial heart valve, by sewing preserved animal tissue to a manmade structure, such as a fabric covered stent structure, a needle 10 is used that is so small that its visibility in a most surgical settings would be so low as to impede a surgeon using the needle. In embodiments, the needle 10 is between 40 mm and 60 mm; 42 mm and 58 mm; 44 mm and 56 mm; 46 mm and 54 mm; 48 mm and 52 mm; and 49 mm and 51 mm long. In embodiments, needle 10 has a midpoint diameter 12 of between 0.3 mm and 0.4 mm; 0.31 mm and 0.39 mm; 0.32 mm and 0.38 mm; 0.33 mm and 0.37 mm; 0.34 mm and 0.36 mm. In embodiments, needle 10 is made of any one of the 300 series stainless steels, including 302 and 304 stainless steel. In embodiments, needle 10 has a volume of less than 9 $mm^3$, 8 $mm^3$, 7 $mm^3$, 6 $mm^3$, 5 $mm^3$, and 4 $mm^3$. Further, in embodiments, needle 10 has an external surface area of less than 70 $mm^2$, 65 $mm^2$, 60 $mm^2$, 55 $mm^2$, and 50 $mm^2$. In embodiments, needle 10 has 0.6, 0.55 and 0.5 the strength of a standard industrial needle.

When needle 10 is first introduced into tissue, the point 11 pierces tissue, and the body of needle 10 follows, displacing and thereby damaging tissue. The progress of needle 10 is resisted both due to the tissue displacement and due to the friction between the needle surfaces and the tissue that it is passing through. Accordingly the less displacement, caused by a thinner and lower volume needle, and the less friction, reduced by low friction surfaces of 300 series steel and the smaller surface area of the needle, the more easily the needle 10 can travel through tissue and the less damage it causes. In one embodiment, needle 10 has less than half the flexural strength of a standard industrial needle, but the workers avoid stressing the needle(s) 10 to the point where it breaks or permanently deforms. In one embodiment, the use of the needles reduces repetitive motion work injuries, by reducing the force needed to push the needles 10 through the tissue, and thereby relieving the stress on the workers' muscles, which is a great contributing factor to repetitive work injuries.

In one method embodiment, the work piece, tissue and needle are viewed under a mounted magnifier. In one method this is a magnifying glass mounted on an arm that permits a user to look through the magnifying glass without holding it. In another method, the work piece, tissue and needle are viewed through a microscope. Early results indicate that workers using the specialty needles report lower levels of muscle stress, which is a contributing factor to repetitive motion work injuries.

The disclosed embodiments are illustrative, not restrictive. While specific configurations of the bioprosthetic heart valve manufacturing techniques have been described, it is understood that the present invention can be applied to a wide variety of bioprosthetic device production. There are many alternative ways of implementing the invention.

What is claimed is:

1. A method of sewing preserved animal tissue to a manmade work piece that forms a part of a prospective bioprosthetic heart valve, comprising:
   a) providing a straight needle having an attached suture length, said needle having a relative object visibility of less than 0.8 relative to a standard straight surgical needle, and that has a volume of less than 7 $mm^3$ and a surface area of less than 70 $mm^2$, and is formed entirely of 300 series stainless steel, said needle having an eye and said suture length being threaded through said eye; and
   b) using said needle having an attached suture length to manually sew said animal tissue to said manmade work piece that forms a part of said prospective bioprosthetic heart valve, while maintaining sufficient optical closeness to maintain the visibility of the needle.

2. The method of claim 1, wherein said needle has a bottom defined by a point and an opposed top, and wherein said top defines an oval shape when viewed from above.

3. The method of claim 2, wherein said needle becomes increasingly round as it extends from top to bottom.

4. The method of claim 1, wherein said needle has a surface area of less than 65 mm$^2$.

5. The method of claim 1, wherein said needle has a surface area of less than 55 mm$^2$.

6. The method of claim 1, wherein said needle has a surface area of less than 50 mm$^2$.

7. The method of claim 1, wherein said needle is made of 302 stainless steel.

8. The method of claim 1, wherein said needle is made of 304 stainless steel.

9. The method of claim 1, wherein said work piece, tissue and needle are viewed under a mounted magnifier.

10. A method of sewing preserved animal tissue to a manmade structure, in the production of a bioprosthetic heart valve, comprising:
   a) providing a needle having an attached suture length, said needle having a relative flexural strength of less than half that of a standard industrial needle, and has a volume of less than 7 mm$^3$ and a surface area of less than 70 mm$^2$; and
   b) using said needle having an attached suture length to manually sew said animal tissue to said manmade work piece that forms a part of said prospective bioprosthetic heart valve, while not placing so much flexural stress on said needle that said flexural stress causes said needle to permanently deform or break.

11. The method of claim 10, wherein said needle has a has a top that defines an oval shape, when viewed from above, and when the point of the needle is considered to be the bottom.

12. The method of claim 11, wherein said needle becomes increasingly round as it extends from top to bottom.

13. The method of claim 10, wherein said needle has a surface area of less than 60 mm$^2$.

14. The method of claim 10, wherein said needle has a surface area of less than 50 mm$^2$.

15. The method of claim 10, wherein said needle is made of 302 stainless steel.

16. The method of claim 10, wherein said needle is made of 304 stainless steel.

17. A method of reducing incidence of repetitive motion work injuries among workers sewing together artificial heart valves from preserved animal tissue and manmade materials and experiencing muscle stress, as a consequence, said method comprising:
   a) providing needles which have a relative visibility of less than 0.8 that of standard surgical needles and less than half the strength of standard industrial needles, and having a volume of less than 7 mm$^3$;
   b) having said workers use said needles in sewing said bioprosthetic heart valves while maintaining sufficient optical closeness to ensure needle visibility and not stressing said needles so much that they permanently deform or break;
   c) wherein said relatively smaller volume of said needles reduces the force needed to push said needles through said preserved animal tissue, thereby reducing repetitive motion work injuries.

18. The method of claim 17, wherein said needle has a top that defines an oval shape, when viewed from above, and when the point of the needle is considered to be the bottom.

19. The method of claim 17, wherein said needle has a surface area of less than 60 mm$^2$ becomes increasingly round as it extends from top to bottom.

20. The method of claim 17, wherein said needle is made of 302 stainless steel.

\* \* \* \* \*